US010441151B2

United States Patent
Ikeda et al.

(10) Patent No.: US 10,441,151 B2
(45) Date of Patent: Oct. 15, 2019

(54) ENDOSCOPE

(71) Applicant: FUJIFILM Corporation, Tokyo (JP)

(72) Inventors: Toshiyuki Ikeda, Kanagawa (JP);
Tomohiro Ohki, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 362 days.

(21) Appl. No.: 15/344,930

(22) Filed: Nov. 7, 2016

(65) Prior Publication Data

US 2017/0049308 A1 Feb. 23, 2017

Related U.S. Application Data

(63) Continuation of application No. 14/068,949, filed on Oct. 31, 2013, now Pat. No. 9,521,948, which is a (Continued)

(30) Foreign Application Priority Data

Mar. 1, 2011 (JP) .................................. 2011-043848

(51) Int. Cl.
*A61B 1/12* (2006.01)
*A61B 1/00* (2006.01)
(Continued)

(52) U.S. Cl.
CPC .......... *A61B 1/126* (2013.01); *A61B 1/00091* (2013.01); *A61B 1/00119* (2013.01);
(Continued)

(58) Field of Classification Search
CPC ........................ A61B 1/00091; A61B 1/126
(Continued)

(56) References Cited

U.S. PATENT DOCUMENTS 5,674,182 A * 10/1997 Suzuki ............... A61B 1/00057
600/121
6,976,957 B1 12/2005 Chin
(Continued)

FOREIGN PATENT DOCUMENTS

CN 101137319 A 3/2008
CN 101156767 A 4/2008
(Continued)

OTHER PUBLICATIONS

EPO Office Communication pursuant to Article 94(3) EPC, dated Feb. 6, 2018, in European Application No. 13 190 126.6-1124 (English version thereof).
(Continued)

*Primary Examiner* — Alexandra L Newton
*Assistant Examiner* — Rynae Boler
(74) *Attorney, Agent, or Firm* — McGinn I.P. Law Group, PLLC.

(57) ABSTRACT

An endoscope includes a first flat surface formed at a distal end portion of an insertion part to be inserted into a subject, and orthogonal to an axial direction of the insertion part, an observation window provided at the distal end portion for allowing image light of the subject to be taken therethrough, with a surface of the observation window as a light incidence plane, an illumination window provided at the distal end portion to irradiate a subject with illumination light, a fluid jetting nozzle arranged at the first flat surface to jet a fluid toward the observation window and fixed at the distal end portion of the insertion part, and an inclined surface formed around the observation window and arranged at a position that faces the fluid jetting nozzle.

9 Claims, 12 Drawing Sheets

Related U.S. Application Data continuation of application No. 13/403,133, filed on Feb. 23, 2012, now Pat. No. 8,777,845.

(51) Int. Cl.
    *A61B 1/05*     (2006.01)
    *A61B 1/018*     (2006.01)
    *A61B 1/06*     (2006.01)
    *A61B 1/07*     (2006.01)

(52) U.S. Cl.
    CPC .............. *A61B 1/018* (2013.01); *A61B 1/051* (2013.01); *A61B 1/0669* (2013.01); *A61B 1/07* (2013.01); *A61B 1/12* (2013.01); *A61B 1/127* (2013.01); *A61B 1/0676* (2013.01)

(58) Field of Classification Search
    USPC .................................................. 600/129, 157
    See application file for complete search history.

(56) References Cited

U.S. PATENT DOCUMENTS

2006/0161047 A1*  7/2006  Miyoshi ............. A61B 1/00091
    600/157
2009/0093681 A1    4/2009  Ichimura
2009/0253966 A1*  10/2009  Ichimura .............. A61B 1/0008
    600/175
2011/0112363 A1    5/2011  Koga et al.

FOREIGN PATENT DOCUMENTS

| | | |
|---|---|---|
| CN | 101511256 A | 8/2009 |
| EP | 1 665 978 A1 | 6/2006 |
| EP | 1 859 723 A1 | 11/2007 |
| EP | 1 908 392 A1 | 4/2008 |
| EP | 2 057 930 A1 | 5/2009 |
| JP | H 3-56402 U | 5/1991 |
| JP | 2003-210388 A | 7/2003 |
| JP | 2007-330529 A | 12/2007 |

OTHER PUBLICATIONS

Chinese Office Action dated Nov. 27, 2014 with English Translation.
Chinese Office Action dated Oct. 10, 2014 with English Translation.
European Office Communication dated Mar. 14, 2014.
Extended European Search Report dated Jan. 8, 2014.
Extended European Search Report dated May 2, 2012.
Office Action in U.S. Appl. No. 14/068,949 dated Oct. 23, 2015.
Office Action in U.S. Appl. No. 14/068,949 dated Mar. 23, 2016.
Notice of Allowance in U.S. Appl. No. 14/068,949 dated Aug. 4, 2016.

* cited by examiner

ENDOSCOPE

The present application is a Continuation Application of U.S. patent application Ser. No. 14/068,949, filed on Oct. 31, 2013, which is a Continuation Application of U.S. patent application Ser. No. 13/403,133, filed on Feb. 23, 2012, now U.S. Pat. No. 8,777,845 B2, issued on Jul. 15, 2014, which is based on and claims priority from Japanese Patent Application No. 2011-043848, filed on Mar. 1, 2011, the entire contents of which are incorporated herein by reference.

BACKGROUND OF THE INVENTION

1. Field of the Invention

The present invention relates to an endoscope including a fluid jetting nozzle that jets a fluid toward an observation window.

2. Description of the Related Art

An endoscope includes, at a distal end portion of an insertion part to be inserted into a subject, an observation window for allowing image light of the subject to be loaded therethrough, an illumination window for irradiating the subject with illumination light, and a fluid jetting (air supply and water supply) nozzle that jets a fluid (washing water or air) toward the observation window. The observation window and the fluid jetting nozzle are arranged on a flat surface orthogonal to an axial direction of the insertion part. Additionally, the pair of illumination windows is arranged at positions substantially symmetrical with respect to the observation window.

In the related art, it is general that the surface of the observation window that becomes a light incidence plane is arranged substantially in the same plane as the flat surface of the insertion part. Since a liquid or dirt within a subject adheres to the surface of the observation window, water is jetted from a jetting port of the fluid jetting nozzle to flush the dirt from the observation window, and air is jetted from the jetting port to blow away waterdrops remaining on the surface of the observation window. Since observation is not easily performed if dirt or waterdrops remain on a portion of the observation window, a fluid jetted from the fluid jetting nozzle preferably spreads over the entire surface of the observation window.

For this reason, in an endoscope described in JP2003-210388A, the surface of an observation window is disposed so as to protrude by a predetermined height with respect to the flat surface of an insertion part, and an inclined portion that inclines such that the height thereof becomes larger gradually toward the surface of an observation window from the flat surface is formed over the entire circumference of a peripheral edge of the observation window. Since a fluid jetted from a jetting port of a fluid jetting nozzle collides with an inclined surface of the inclined portion and flows smoothly toward the surface of the observation window, the fluid can be spread on the entire surface of the observation window. The fluid passed through the surface of the observation window flows down an inclined surface opposite to the fluid jetting nozzle, and flows to the flat surface. By providing the inclined portion in this way, the cleanability of the observation window, and removal of water to be jetted is improved. Additionally, in an endoscope described in JP2007-330529A, a distal end face of a protruding stepped portion (stepped portion) that protrudes by a predetermined height from a flat surface is provided with an observation window, a wall portion of the protruding stepped portion is formed with an inclined surface, and a fluid jetting nozzle is arranged so as to face this inclined surface. This enables a fluid to be applied to an inclined surface so as to guide the fluid to the observation window.

SUMMARY OF THE INVENTION

An object of the present invention is to provide an endoscope that reliably guides a fluid to an observation window so as to allow washing.

An endoscope of the present invention includes a first flat surface formed at a distal end portion of an insertion part to be inserted into a subject, and orthogonal to an axial direction of the insertion part, an observation window provided at the distal end portion for allowing image light of the subject to be taken therethrough, with a surface of the observation window as a light incidence plane, an illumination window provided at the distal end portion to irradiate a subject with illumination light, a fluid jetting nozzle arranged at the first flat surface to jet a fluid toward the observation window and fixed at the distal end portion of the insertion part, and an inclined surface formed around the observation window and arranged at a position that faces the fluid jetting nozzle, wherein the distal end portion is formed with a second flat surface arranged on the distal end side of the first flat surface and parallel to the first flat surface, wherein the inclined surface includes a surface that connects the first flat surface and the second flat surface together, wherein the illumination window is arranged at the second flat surface, wherein the surface of the observation window is disposed so as to protrude by a predetermined distance from the second flat surface, wherein a top of the fluid jetting nozzle in the axial direction is disposed at the topmost side in the axial direction, and wherein the jetting nozzle includes a jetting port from which the fluid is jetted and a part of the jetting port is disposed on the distal end side with respect to the surface of the observation window in the axial direction.

According to the endoscope of an exemplary aspect of the present invention, a fluid can be reliably guided to the observation window so as to perform washing.

DESCRIPTION OF THE PREFERRED EMBODIMENTS

Figure 1:
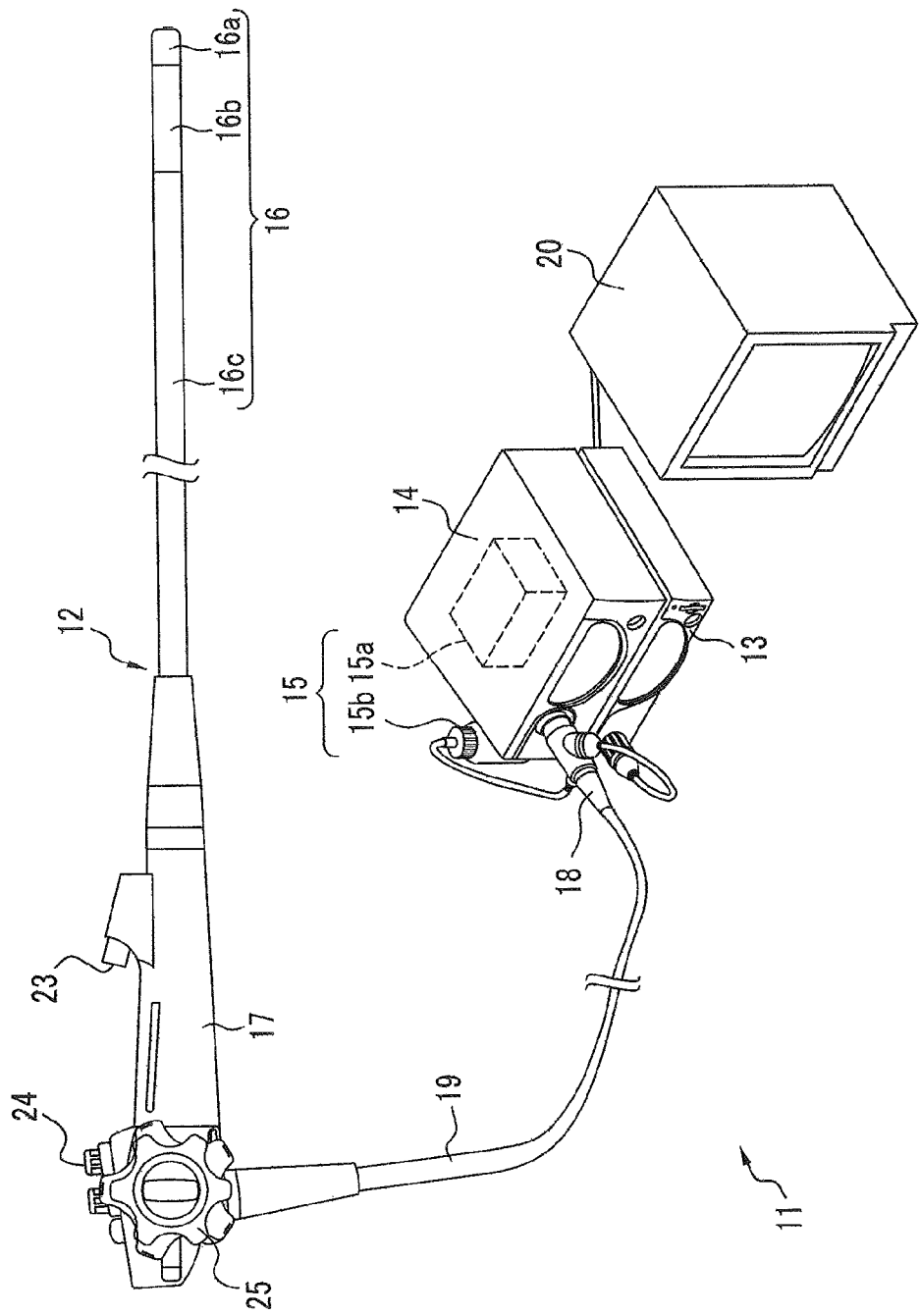
FIG. 1 is a perspective view showing the appearance of an endoscope system.

As shown in FIG. 1, an electronic endoscope system 11 includes an electronic endoscope 12, a processor device 13, a light source device 14, an air supply and water supply device 15, or the like. The air supply and water supply device 15 includes a widely-known air supply device (pump or the like.) 15a that is built in the light source device 14 and that performs air supply, and a washing water tank 15b that is provided outside the light source device 14 and stores washing water. The electronic endoscope 12 has a flexible insertion part 16 to be inserted into the body of a subject, a manipulating part 17 connected to a proximal end portion of the insertion part 16, a connector 18 connected to the processor device 13 and the light source device 14, and a universal cord 19 connecting the manipulation part 17 and the connector 18 together. The connector 18 is a complex connector, and has the processor device 13 and the light source device 14, and air supply and water supply device 15 connected thereto, respectively.

The insertion part 16 includes a distal end portion 16a provided at a distal end thereof and having a CCD type image sensor 40 (refer to FIG. 2, hereinafter referred to as CCD) as an imaging element for photographing the inside of a subject or the like built therein, a bending portion 16b connected to a proximal end of the distal end portion 16a, and a flexible tube portion 16c connected to a proximal end of the flexible bending portion 16b. Hereinafter, the distal end of the insertion part 16 is simply referred to as the "distal end", and the proximal end of the insertion part 16 is simply referred to as the "proximal end".

The processor device 13 is electrically connected to the light source device 14, and controls the operation of the electronic endoscope system 11 in general. The processor device 13 supplies electric power to the electronic endoscope 12 through a transmission cable inserted through the universal cord 19 or the insertion part 16, and controls the driving of the CCD 40. Additionally, the processor device 13 acquires an imaging signal output from the CCD 40 through the transmission cable, and performs various kinds of image processing to generate image data. The image data generated by the processor device 13 is displayed as an observation image on a monitor 20 cable-connected to the processor device 13.

The air supply and water supply channel 21 (refer to FIG. 3) is disposed inside the insertion part 16 and the manipulating part 17, and the air supply and water supply channel 21 is connected to an air supply and water supply nozzle (fluid jetting nozzle) 22 (refer to FIGS. 2 to 4) provided at the distal end portion 16a. Additionally, the air supply and water supply channel 21 is connected to the air supply and water supply device 15 through the universal cord 19.

The manipulating part 17 is provided with a forceps port 23 through which various treatment tools having an injection needle, a surgical knife, or the like disposed at the distal end thereof, are inserted, an air supply and water supply button 24, an angle knob 25, or the like. If air supply manipulation is performed by pushing the air supply and water supply button 24, the air generated by the air supply device 15a is sent to the air supply and water supply nozzle 22, and if water supply manipulation is performed, washing water is sent to the air supply and water supply nozzle 22 from the washing water tank 15b by the pressure of the air generated by the air supply device 15a. The air supply and water supply nozzle 22 selectively jets the air and washing water supplied through the air supply and water supply channel 21.

Additionally, if the angle knob 25 is manipulated, the bending portion 16b operates to be curved up and down and right and left as a wire provided to be inserted into the insertion part 16 is pushed or pulled. This causes the distal end portion 16a to be directed in a desired direction within a body cavity.

Figure 2:
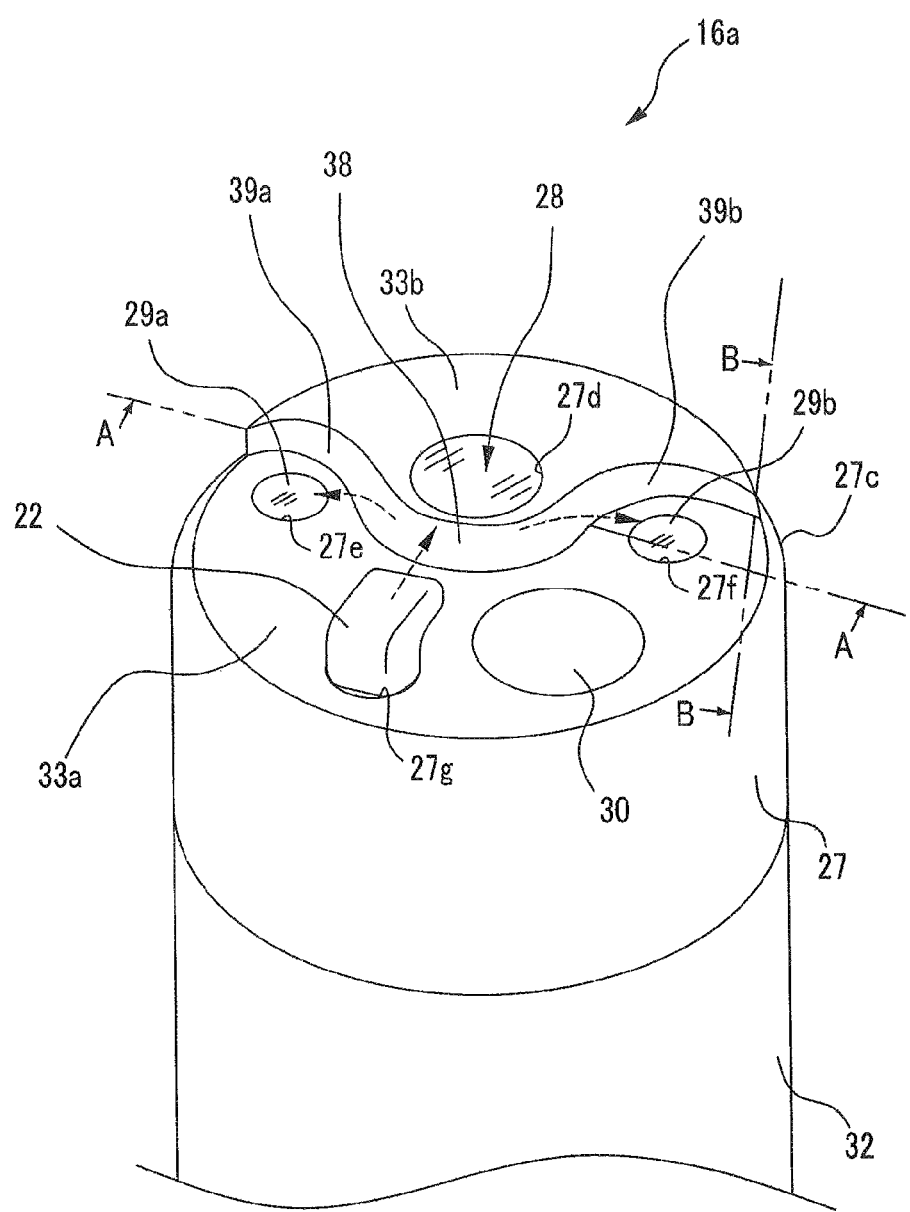
FIG. 2 is a perspective view showing the configuration of a distal end portion of an insertion part.
Figure 3:
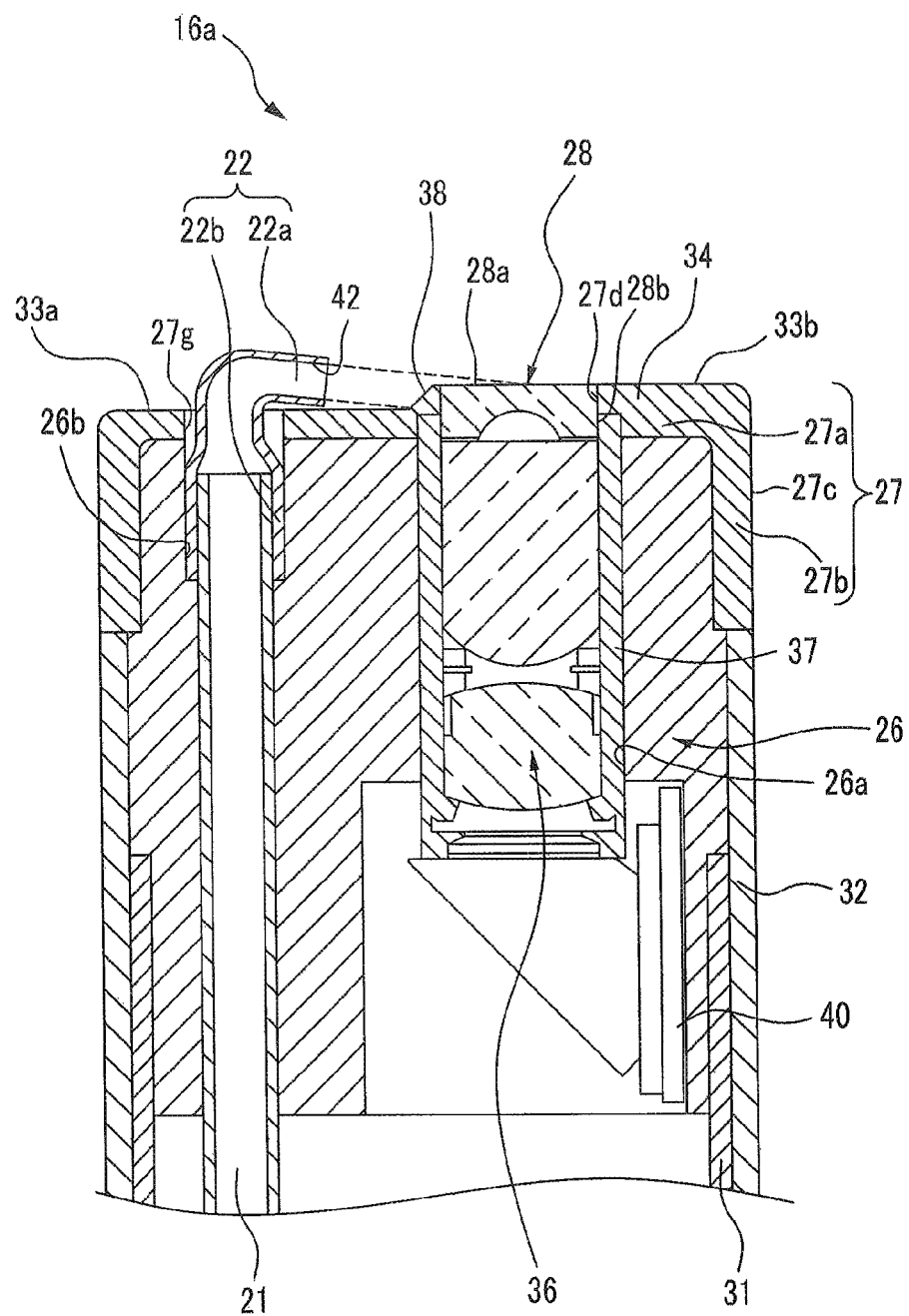
FIG. 3 is a cross-sectional view of the distal end portion along an observation window and a fluid jetting nozzle.
Figure 4:
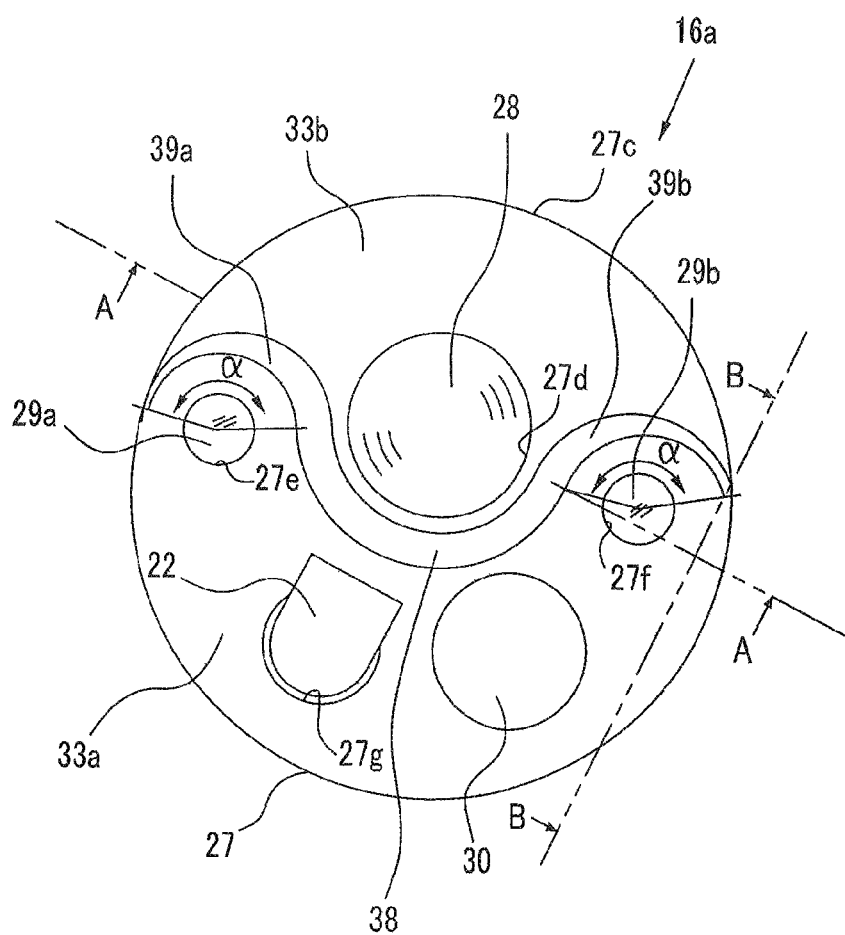
FIG. 4 is a plan view of the distal end portion showing the positional relationship of a fluid guide surface.
Figure 5A:
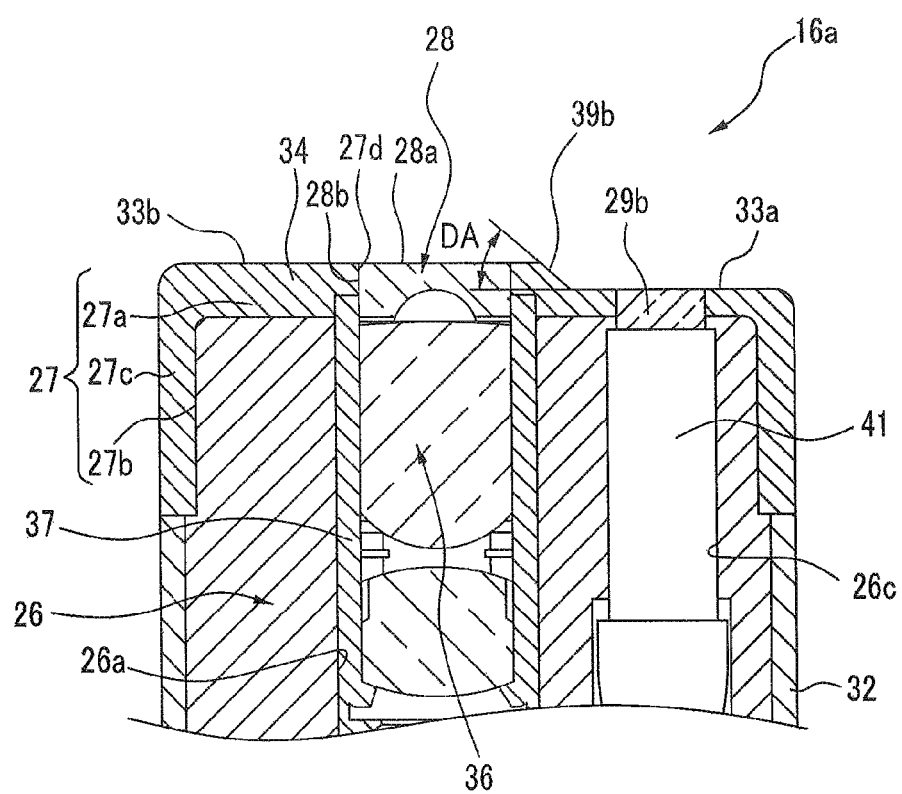
FIGS. 5A and 5B are cross-sectional views of a cutting plane (A) shown by a line A-A of FIGS. 2 and 4 and a cutting plane (B) shown by a line B-B.
Figure 5B:
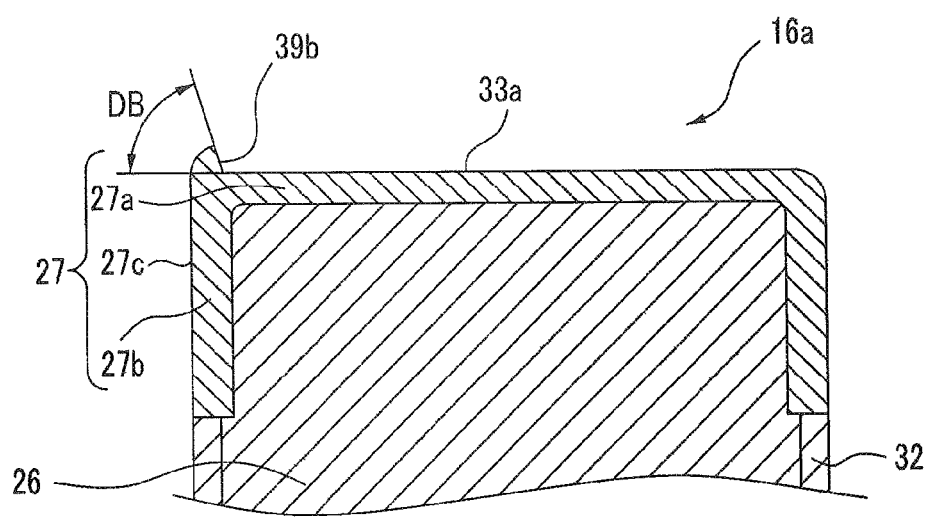

As shown in FIGS. 2, 3, and 4, the distal end portion 16a includes a distal end portion body 26, a cap-shaped distal end protective cap 27 mounted on the distal end of the distal end portion body 26, observation windows 28, two illumination windows 29a and 29b, forceps outlet 30, and the air supply and water supply nozzle 22. In the distal end portion body 26, through holes 26a to 26c each of which holds respective parts, such as the air supply and water supply nozzle 22, an objective lens unit 36 to be described below, and a light guide 41 (refer to FIG. 5), are formed along the axial direction of the insertion part 16. A rear end of the distal end portion body 26 is coupled to a bending piece 31 at the distal end that constitutes the bending portion 16b.

The distal end protective cap 27 includes a distal end plate portion 27a that covers the distal end of the distal end portion body 26, and a cylindrical portion 27b that covers the outer peripheral surface of the distal end portion body 26. An envelope layer 32 that covers the outer peripheral surface of the bending portion 16b extends up to the distal end portion body 26, and the distal end of the envelope layer 32 and the rear end of the cylindrical portion 27b are butted against each other whereby the ends are fastened to each other with an adhesive or the like. The distal end plate portion 27a is formed with a planar, first flat surface 33a orthogonal to the axial direction of the insertion part 16.

The distal end plate portion 27a is formed with a stepped portion 34 that protrudes toward the distal end with respect to the first flat surface 33a.

The stepped portion 34 extends to the opposite side of the air supply and water supply nozzle 22 from near the center of the distal end plate portion 27a, and is continuous with an outer peripheral surface of the distal end plate portion 27a, that is, an outer peripheral surface 27c of the distal end protective cap 27. A distal end of the stepped portion 34 is formed with a second flat surface 33b arranged parallel to the first flat surface 33a.

The distal end plate portion 27a is formed with through holes 27d to 27g that expose the observation window 28, the illumination windows 29a and 29b, and the air supply and water supply nozzle 22, when the first and second flat surfaces 33a and 33b are seen from the distal end, and the forceps outlet 30. The observation window 28 is arranged at a position surrounded by the vicinity of the center of the distal end portion 16a and the second flat surface 33b. Additionally, the pair of illumination windows 29a and 29b is arranged at positions symmetrical with respect to the observation window 28.

The observation window 28 is an objective lens on the tip side that constitutes the objective lens unit 36, and serves also as a cover glass. The observation window 28 has a substantially disc-shaped appearance, and has a surface 28a that is a light incidence plane, and an outer peripheral surface 28b continuous with the surface 28a.

The optical system of the objective lens unit 36 including the observation window 28 is held by a lens barrel 37. The lens barrel 37 holds the proximal end of the outer peripheral surface 28b of the observation window 28. The distal end of the outer peripheral surface 28b of the observation window 28 fits into the through hole 27d of the distal end protective cap 27. The lens barrel 37 fits into the through hole 26a of the distal end portion body 26, and the distal end face thereof is butted against and attached to the distal end plate portion 27a of the distal end protective cap 27.

The observation window 28 is attached at a position where the surface 28a becomes flush with the second flat surface 33b. In the distal end protective cap 27, an inclined surface 38 is formed around the observation window 28. The inclined surface 38 connects the first flat surface 33a and the second flat surface 33b together, is reduced in height gradually toward the first flat surface 33a from the second flat surface 33b, and inclines toward the proximal end from the distal end. Moreover, the inclined surface 38 is formed in the shape of a taper that surrounds approximately the half circumference of the entire circumference of the observation window 28 that faces the air supply and water supply nozzle 22. In addition, the range in which the inclined surface 38 is formed is not limited to this, and may be arranged at least at a position that faces the air supply and water supply nozzle 22.

Moreover, in the distal end protective cap 27, fluid guide surfaces 39a and 39b arranged so as to extend to the perimeter of the illumination windows 29a and 29b, are arranged on both sides of the inclined surface 38, respectively. The fluid guide surfaces 39a and 39b connects the first flat surface 33a and the second flat surface 33b together, and are smoothly continuous with the inclined surface 38. The fluid guide surfaces 39a and 39b incline toward the proximal end from the distal end so as to guide a fluid to the illumination windows 29a and 29b, and is formed in the shape of a mortar that is reduced in height gradually toward the illumination windows 29a and 29b.

A CCD 40 is attached to a deep portion of the objective lens unit 36. The CCD 40 includes, for example, an interline transfer type CCD, and a subject image loaded by the optical system of the objective lens unit 36 is formed on an imaging surface. In addition, the imaging element is not limited to the CCD 40, and may be a type of CMOS.

The illumination windows 29a and 29b serve also as exposure lenses, and irradiate at least the portion to be observed within a subject with illumination light from the light source device 14. The illumination windows 29a and 29b are attached at positions where the surfaces (distal end faces) thereof become flush with the first flat surface 33a, and face an outgoing end of the light guide 41. The light guide 41 is formed by bundling a number of optical fibers (for example, made of silica based glass), externally fitting a ferrule at the distal end thereof, and covers an outer peripheral surface thereof with a tube. The light guide 41 passes through the insides of the insertion part 16, the manipulating part 17, the universal cord 19, and the connector 18, and guides the illumination light from the light source device 14 to the illumination windows 29a and 29b. The forceps outlet 30 is connected to a forceps channel (not shown) disposed within the insertion part 16, and communicates with the forceps port 23 of the manipulating part 17. Various treatment tools inserted through the forceps port 23 has distal ends exposed from the forceps outlet 30.

As for the air supply and water supply nozzle 22, a jetting cylinder portion 22a on the distal end and a connection cylinder portion 22b on the proximal end are integrally formed. The connection cylinder portion 22b is fitted to a distal-end-side outer peripheral surface of the air supply and water supply channel 21, and is connected to the air supply and water supply channel 21. Additionally, the connection cylinder portion 22b, and the air supply and water supply channel 21 are fitted to a through hole 26b of the distal end portion body 26. The jetting cylinder portion 22a is formed in the shape of a cylinder smoothly bent to a jetting port 42 at a distal end thereof from the connection cylinder portion 22b, and is exposed to the outside through the through hole 27g of the distal end protective cap 27.

Moreover, a fluid jet range using the air supply and water supply nozzle 22 is preferably set such that a fluid is applied to at least the inclined surface 38, preferably, such that a fluid is applied to both the observation window 28 and the inclined surface 38.

The arrangement of the fluid guide surfaces 39a and 39b will be described with reference to FIGS. 4 and 5. Symbol a represents the angle range of the fluid guide surfaces 39a and 39b surrounding the illumination windows 29a and 29b, and this angle range α is 120° or more. That is, the fluid guide surfaces 39a and 39b are arranged at positions where the fluid guide surfaces surround ⅓ or more of the entire circumferences of the illumination windows 29a and 29b.

Additionally, symbol DA (refer to FIG. 5A) and symbol DB (refer to FIG. 5B) represent the rising angle (the angle of the generating line of the fluid guide surface 39b) of the fluid guide surface 39b with respect to the first flat surface 33a. Moreover, the rising angle DA is the rising angle of the fluid guide surface 39b at a position that touches the inclined surface 38, and the rising angle DB is the rising angle of the fluid guide surface 39b at a position that touches the outer peripheral surface 27c. The fluid guide surface 39b is formed such that the rising angle thereof becomes larger gradually toward the outer peripheral surface 27c from the central side of the distal end portion 16a. That is, the fluid guide surface 39b is formed such that the rising angle DA at the position that touches the inclined surface 38 becomes the smallest and the rising angle DB at the position that touches the outer peripheral surface 27c becomes the largest. In addition, the fluid guide surface 39a is also formed similarly to the fluid guide surface 39b such that the rising angle thereof becomes larger gradually toward the outer peripheral surface 27c from the central side of the distal end portion 16a. Thereby, the fluid that impacts against the observation window 28 or the inclined surface 38 and is guided to the fluid guide surfaces 39a and 39b is stopped by the fluid guide surfaces 39a and 39b near the outer peripheral surface 27c, and easily flows to the illumination windows 29a and 29b.

The process when the washing of the observation window 28 by the fluid jetting of the air supply and water supply nozzle 22 is performed using the electronic endoscope 12 of the above configuration will be described. A portion of the fluid (air or washing water) jetted from the air supply and water supply nozzle 22 impact against the inclined surface 38. While the fluid that impacts against the inclined surface 38 spreads in the circumferential direction of the observation window 28, the fluid climbs up the inclined surface 38. Thereby, the fluid spreads over the entire surface 28a of the observation window 28, and a liquid or dirt adhering to the surface 28a are blown away. Moreover, washing water is also blown away by the jetting of air.

Most of the fluid (air or washing water) that rides over the observation window 28 and the inclined surface 38 flows down along the fluid guide surfaces 39a and 39b. Since the fluid jetted from the air supply and water supply nozzle 22 in this way can be guided to the inclined surface 38 so as to sufficiently wash the observation window 28, and the fluid that rides over the observation window 28 and the inclined surface 38 is guided to the fluid guide surfaces 39a and 39b, the washing of the illumination windows 29a and 29b can also be performed.

As described above, since the fluid guide surfaces 39a and 39b are formed such that the rising angles thereof becomes larger gradually toward the outer peripheral surface 27c from the central side of the distal end portion 16a, the fluid easily flows to the illumination windows 29a and 29b. Moreover, since the fluid guide surfaces 39a and 39b are arranged so as to surround the illumination windows 29a and 29b, a fluid easily flow to the illumination windows 29a and 29b, and cleanability can be improved.

Figure 6:
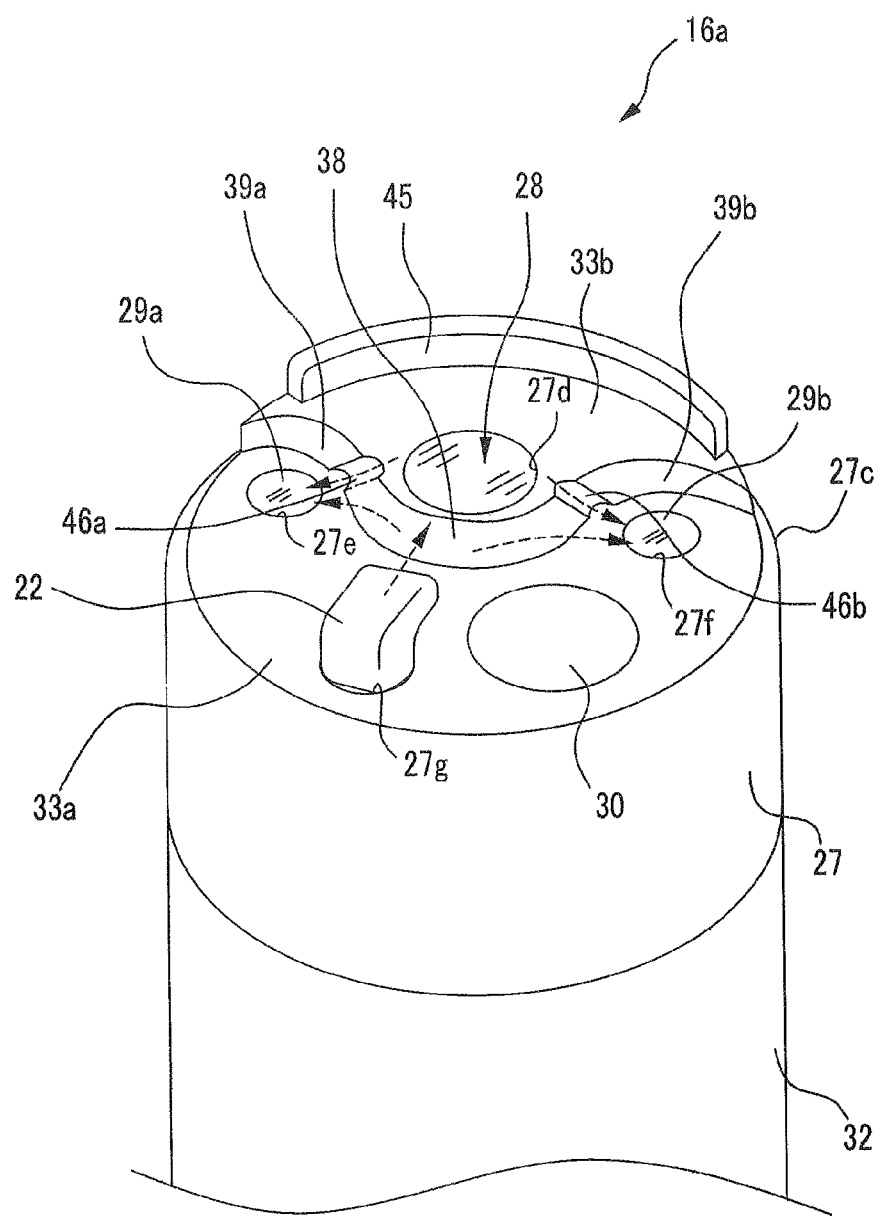
FIG. 6 is a perspective view showing a modification of a first embodiment in which an embankment-shaped protruding portion and a guide groove are formed.

Additionally, as a modification of the above first embodiment, as shown in FIG. 6, a bank-shaped protruding portion 45 may be provided at a position opposite to the air supply and water supply nozzle 22 with the observation window 28 therebetween. In addition, the protruding portion 45 preferably protrudes from the second flat surface 33b to the distal end, and is formed in the shape of a circular arc along the outer peripheral surface 27c. In this case, the fluid that is jetted from the air supply and water supply nozzle 22 and rides over the inclined surface 38 and the observation window 28 impacts against the protruding portion 45. Thereby, since the fluid that impacts against and rebounded from the protruding portion 45 flows down along the second flat surface 33b and the fluid guide surfaces 39a and 39b, the fluid easily flows to the illumination windows 29a and 29b. Moreover, portions of the fluid guide surfaces 39a and 39b may be cut away to form guide grooves 46a and 46b that guide a fluid toward the illumination windows 29a and 29b from the perimeter of the observation window 28 may be formed. A fluid more easily flow to the illumination windows 29a and 29b by the guide grooves 46a and 46b, and cleanability can be improved.

Figure 7:
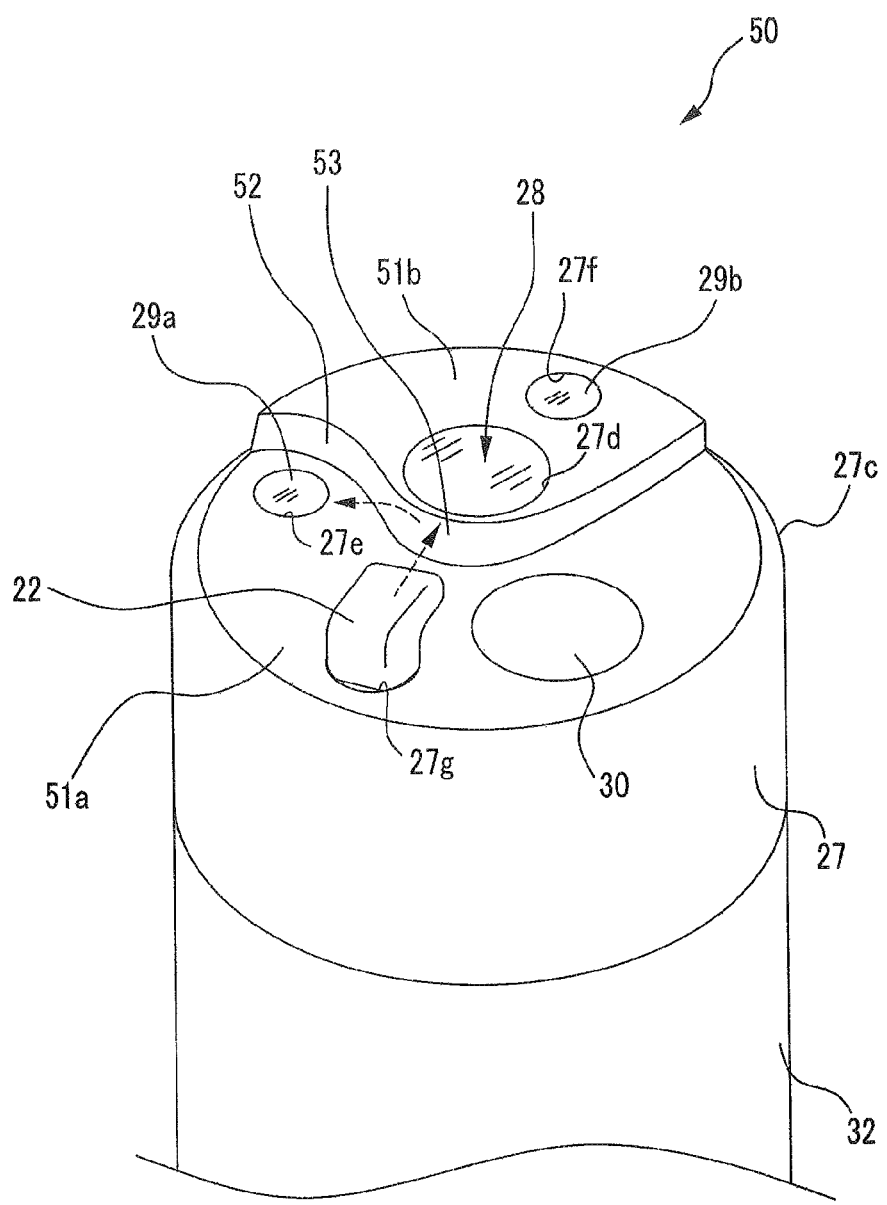
FIG. 7 is a perspective view showing a distal end portion of a second embodiment in which a fluid guide surface that guides a fluid only to one illumination window is formed.
Figure 8:
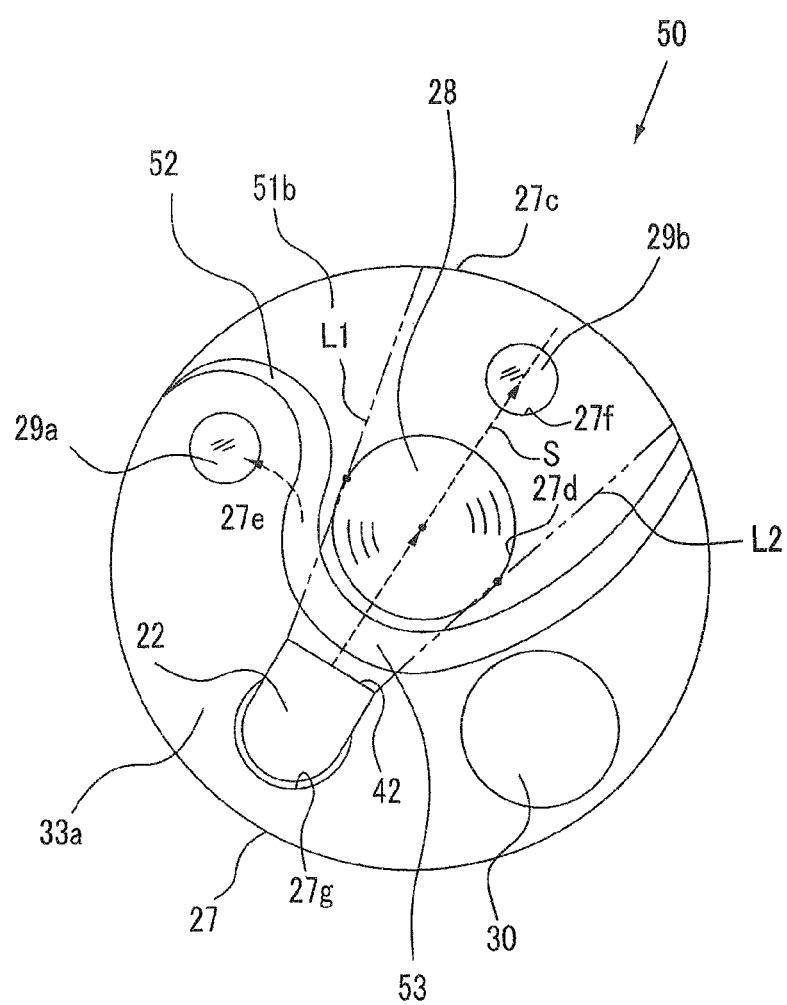
FIG. 8 is a plan view showing a distal end portion of the second embodiment.

In the above first embodiment, both of the illumination windows 29a and 29b are arranged at the first flat surface 33a, and the fluid guide surfaces 39a and 39b that guide a fluid to the illumination windows 29a and 29b, respectively are formed. However, the present invention is not limited to this. As in a distal end portion 50 of a second embodiment shown in FIGS. 7 and 8, one illumination window 29a of the pair of illumination windows 29a and 29b may be arranged at a first flat surface 51a and the other illumination window 29b may be arranged at a second flat surface 51b. Additionally, a fluid guide surface 52 that guide a fluid to the illumination window 29a may be formed, and the illumination window 29b may be arranged within a jetting range of the air supply and water supply nozzle 22. In addition, in FIGS. 7 and 8, those using the same parts as the above first embodiment will be designated by the same reference numerals, and the description thereof will be omitted.

In this second embodiment, the first and second flat surfaces 51a and 51b are formed at the distal end protective cap 27 similarly to the flat surfaces 33a and 33b of the above first embodiment, and are parallel to each other, and the second flat surface 51b are arranged closer to the distal end than the first flat surface 51a. In addition, an inclined surface 53 that connects the first and second flat surfaces 51a and 51b together is formed around the observation window 28. The surface 28a of the observation window 28, is arranged on the same plane as the second flat surface 51b. The inclined surface 53 is arranged at a position that faces the air supply and water supply nozzle 22, similarly to the inclined surface 38 of the above first embodiment.

Additionally, the fluid guide surface 52 connects the first flat surface 51a and the second flat surface 51b together, and is smoothly continuous with the inclined surface 53. Preferably, the fluid guide surface 52, similarly to the fluid guide surfaces 39a and 39b of the above first embodiment, is formed in the shape of a mortar that is reduced in height gradually toward the illumination window 29a and is inclined toward the proximal end from the distal end. Moreover, the air supply and water supply nozzle 22, the observation window 28, and the illumination window 29b are preferably arranged substantially in the shape of a straight line along a jetting direction S of the air supply and water supply nozzle 22 (refer to FIG. 8). Specifically, the jetting direction S is located on a straight line passing through the center of the jetting port 42 of the air supply and water supply nozzle 22, and the center of the observation window 28, and the illumination window 29b is located on the downstream side of the observation window 28 in the jetting direction S. Additionally, symbols L1 and L2 represent two straight lines that do not cross a straight line passing through the jetting direction S at positions closer to the downstream side than the air supply and water supply nozzle 22 and that pass through both ends of the jetting port 42 of the air supply and water supply nozzle 22, and the peripheral edge of the observation window 28. The illumination window 29b is preferably arranged within a range surrounded by the two straight lines L1 and L2, and most preferably located on an extension line in the jetting direction S. Alternatively, even when the illumination window 29b is not located on the extension line in the jetting direction S, it is preferable to arrange the illumination window 29b within a range surrounded by any one of the straight lines L1 and L2 (refer to FIG. 8) and the extension line in the jetting direction S. Thereby, a fluid can be reliably jetted to the illumination window 29b arranged at the second flat surface 51b.

As described above, in this second embodiment, a fluid is guided to one illumination window 29a by the fluid guide surface 52, and the fluid jetted from the air supply and water supply nozzle 22 is blown against the other illumination window 29b. Thus, the observation window 28 can be sufficiently washed similarly to the above first embodiment, and the washing of the illumination windows 29a and 29b can also be performed.

Figure 9:
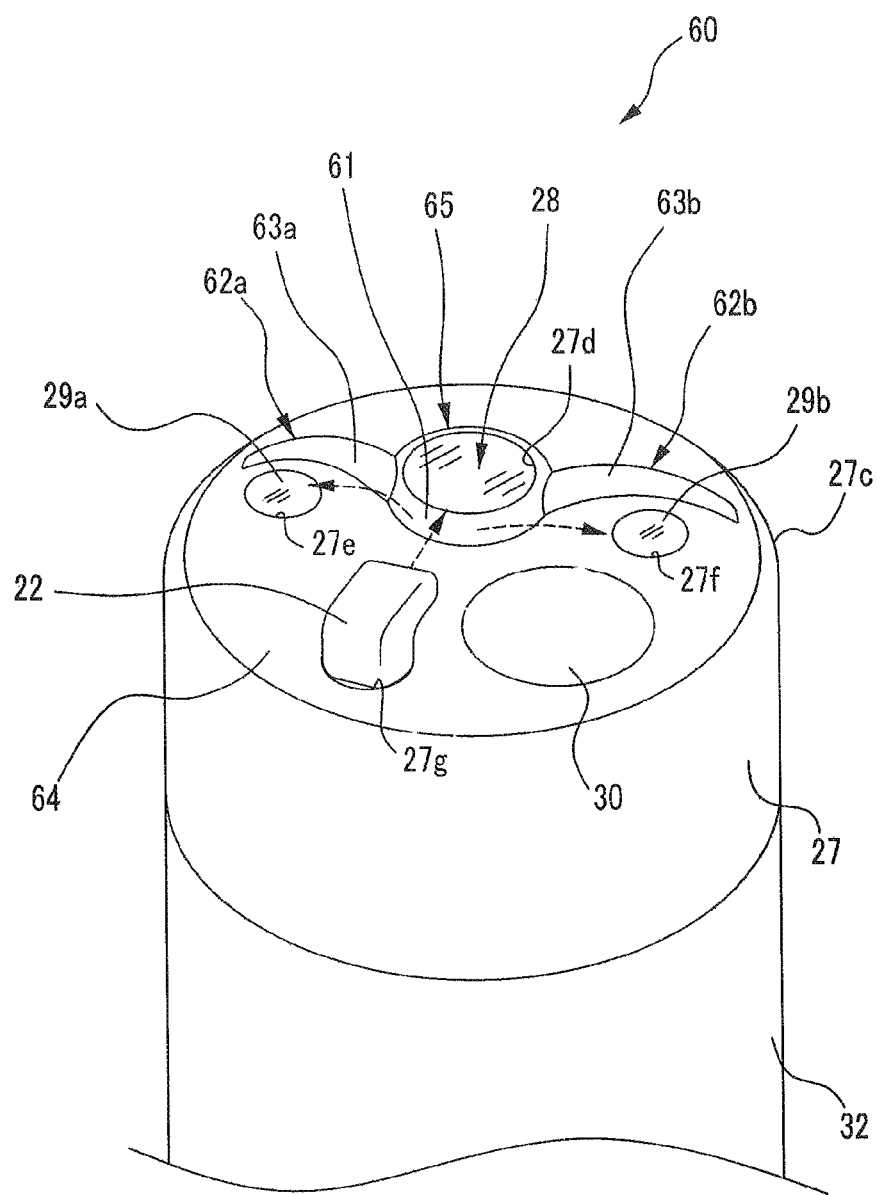
FIG. 9 is a perspective view showing a distal end portion of a third embodiment in which a fluid guide surface is formed at a protruding strip formed so as to extend toward an illumination window from an observation window.
Figure 10:
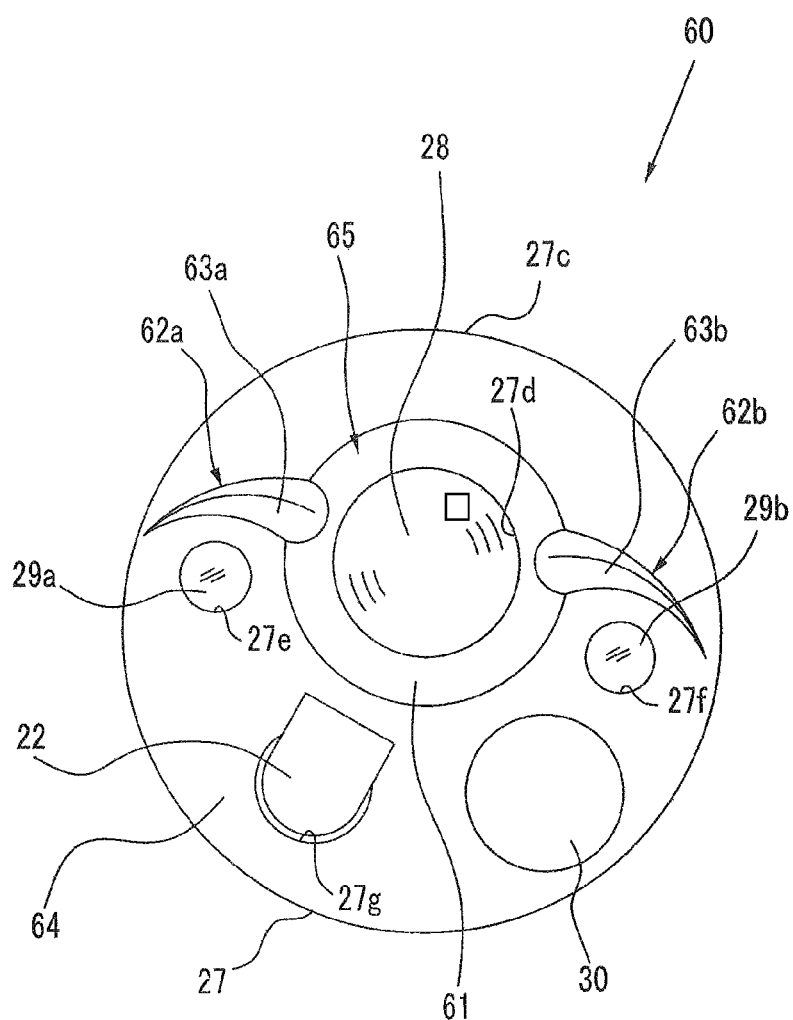
FIG. 10 is a plan view of the distal end portion showing the positional relationship of a fluid jetting nozzle and the perimeter of the observation window.

In the above first and second embodiments, the mutually parallel first and second flat surfaces 33a and 33b or 51a and 51b are arranged at the distal end portion 16a or the distal end portion 50, and the inclined surface 38 or 53 that connects the first flat surface and the second flat surface together and the fluid guide surfaces 39a and 39b or 52 are formed. However, the shapes of the inclined surface and the fluid guide surfaces are not limited to these. As in a distal end portion 60 of a third embodiment shown in FIGS. 9 and 10, an inclined surface 61 may be formed around the observation window 28, and fluid guide surfaces 63a and 63b may be formed at arcuate protruding strips 62a and 62b extending from the observation window 28 to the perimeter of the illumination windows 29a and 29b.

In this third embodiment, an annular protruding portion 65 that protrudes to the distal end from the first flat surface 64 orthogonal to the axial direction of the insertion part 16 and is disposed at the entire circumferences of the observation window 28 is formed, and the inclined surface 61 is formed at an outer peripheral surface of this annular protruding portion 65. In addition, the observation window 28 is attached such that the position of the surface 28a is aligned with the tip position of the annular protruding portion 65. The fluid guide surfaces 63a and 63b are formed at arcuate protruding strips 62a and 62b formed continuously with the annular protruding portion 65. The arcuate protruding strips 62a and 62b are arranged so as to surround the illumination windows 29a and 29b. Preferably, the fluid guide surfaces 63a and 63b, similarly to the fluid guide surfaces 39a and 39b of the above first embodiment, are formed in the shape of a mortar that is reduced in height gradually toward the illumination window 29a and inclines toward the proximal end from the distal end. Additionally, the fluid guide surfaces 63a and 63b are preferably arranged at positions where the fluid guide surfaces surround ⅓ or more of the entire circumferences of the illumination windows 29a and 29b.

Figure 11:
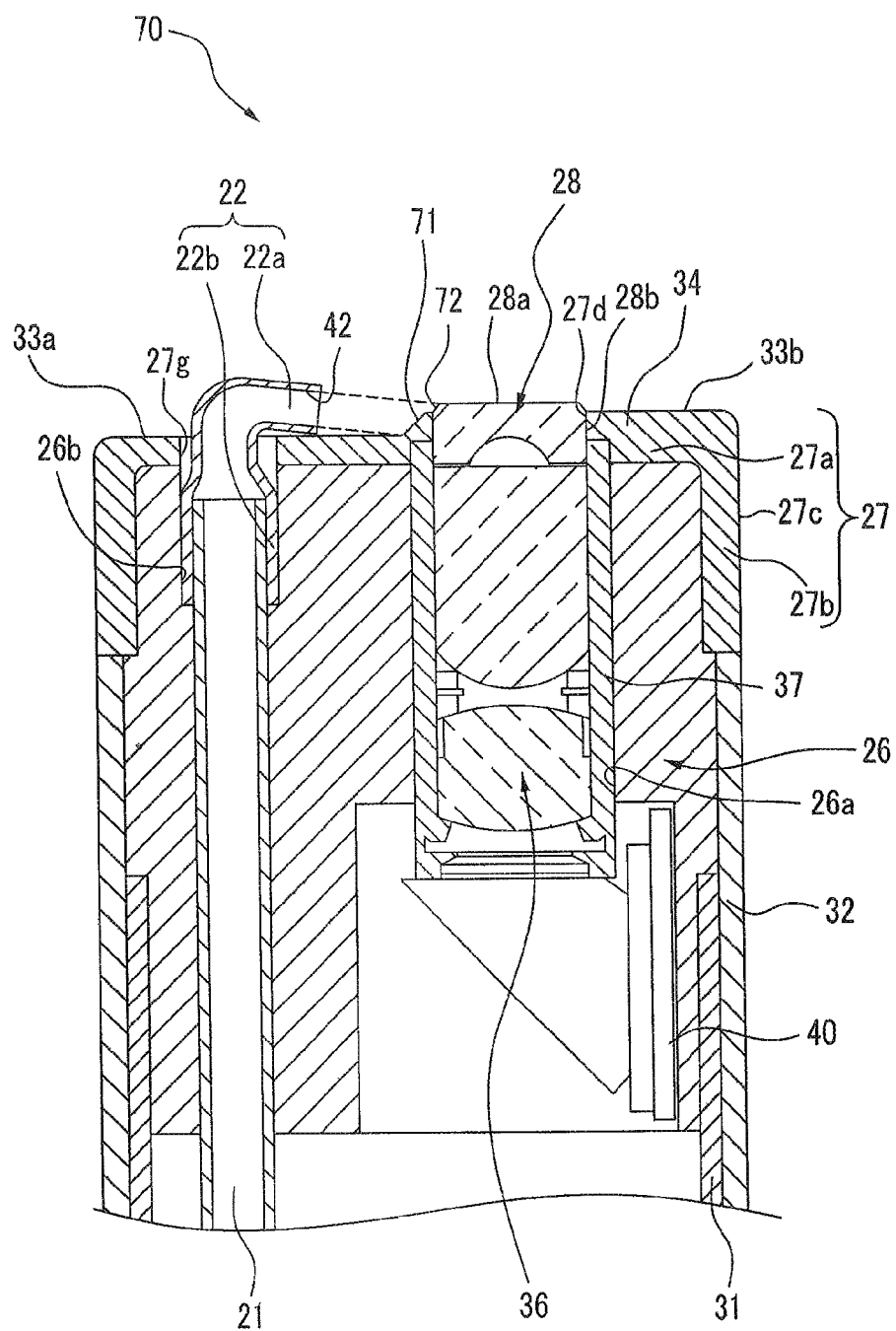
FIG. 11 is a cross-sectional view of essential parts showing an example in which the surface of the observation window is disposed at a position protruding by a predetermined distance from the tip of an inclined surface.

In the above respective embodiments, the surface 28a of the observation window 28 is disposed at the same position as the tips of the second flat surface 33b and 51b or the annular protruding portion 65, that is, the tips of the inclined surfaces 38, 53, and 61. However, the present invention is not limited this. As in a distal end portion 70 shown in FIG. 11, the surface 28a of the observation window 28 may be disposed so as to protrude by a predetermined distance from the tip of the inclined surface 71. Additionally, in the case of the example shown in FIG. 11, it is preferable to form the distal end of the outer peripheral surface 28b of the observation window 28 as a tapered surface 72 that is obliquely cut off. Thereby, the fluid that rides over the inclined surface 71 flows to the surface 28a of the observation window 28 along the tapered surface 72. Additionally, the surface of the observation window 28 is not limited to the flat shape, and may be, for example, a convex lens surface that protrudes to the distal end. In this case, the peripheral edge of the convex lens surface may be arranged at the same position as the tip of the inclined surface 71, or may be arranged so as to protrude by a predetermined distance from the tip of the inclined surface 71.

Additionally, in the above respective embodiments, the fluid guide surfaces 39a, 39b, 52, 63a, and 63b are formed in the shape of a mortar. However, the shape of the fluid guide surfaces is not limited to this. The fluid guide surfaces may be formed in a streamline shape that inclines toward the illumination windows 29a and 29b and has a smooth surface.

Although the electronic endoscope that observes an image obtained by imaging the state of a subject using an imaging device has been described as an example in the above respective embodiments, the present invention is not limited thereto, and can also be applied to an endoscope that adopts an optical image guide to observe the state of a subject.

What is claimed is:

1. An endoscope, comprising:
a first flat surface formed at a distal end portion of an insertion part to be inserted into a subject, and orthogonal to an axial direction of the insertion part;
an observation window provided at the distal end portion for allowing image light of the subject to be taken therethrough, with a surface of the observation window as a light incidence plane;
a forceps outlet disposed on the first flat surface;
a first illumination window provided at the distal end portion to irradiate a subject with illumination light;
a second illumination window provided at the distal end portion to irradiate the subject with illumination light;
a fluid jetting nozzle arranged at the first flat surface to jet a fluid toward the observation window and fixed at the distal end portion of the insertion part; and
an inclined surface formed around the observation window and arranged at a position that faces the fluid jetting nozzle,
wherein the distal end portion is formed with a second flat surface arranged on a distal end side of the first flat surface and parallel to the first flat surface,
wherein the inclined surface is a surface that connects the first flat surface and the second flat surface together,
wherein the first illumination window is arranged at the second flat surface and the second illumination window is arranged at the first flat surface,
wherein the surface of the observation window is disposed so as to protrude by a predetermined distance from the second flat surface,
wherein a top of the fluid jetting nozzle in the axial direction is disposed at the topmost side in the axial direction, and
wherein the jetting nozzle includes a jetting port from which the fluid is jetted and a part of the jetting port is disposed on the distal end side with respect to the surface of the observation window in the axial direction.

2. The endoscope according to claim 1, wherein a position of a part of the jetting port in the axial direction is a same as a position of apart of the inclined surface in the axial direction.

3. The endoscope according to claim 1, wherein a distal end of an outer peripheral surface of the observation window is formed as a tapered surface that is oblique to the axial direction.

4. The endoscope according to claim 2, wherein a distal end of an outer peripheral surface of the observation window is formed as a tapered surface that is oblique to the axial direction.

5. The endoscope according to claim 1, wherein the surface of the observation window includes a flat surface.

6. The endoscope according to claim 2, wherein the surface of the observation window includes a flat surface.

7. The endoscope according to claim 3, wherein the surface of the observation window includes a flat surface.

8. The endoscope according to claim 4, wherein the surface of the observation window includes a flat surface.

9. The endoscope according to claim 1, wherein all constituents disposed at the distal end portion of the insertion part other than the fluid jetting nozzle are disposed on a proximal end side with respect to the top of the fluid jetting nozzle.

* * * * *